(12) United States Patent
Wang

(10) Patent No.: US 6,683,066 B2
(45) Date of Patent: Jan. 27, 2004

(54) COMPOSITION AND TREATMENT METHOD FOR BRAIN AND SPINAL CORD INJURIES

(76) Inventor: Yanming Wang, 203 Summer St., Malden, MA (US) 02148

( * ) Notice: Subject to any disclaimer, the term of this patent is extended or adjusted under 35 U.S.C. 154(b) by 87 days.

(21) Appl. No.: 09/962,009

(22) Filed: Sep. 24, 2001

(65) Prior Publication Data

US 2003/0059476 A1 Mar. 27, 2003

(51) Int. Cl.$^7$ .............................................. A61K 35/78
(52) U.S. Cl. ........................ 514/78; 424/522; 424/523; 424/725; 424/757
(58) Field of Search .......................... 514/78; 424/522, 424/523, 725, 757

(56) References Cited

U.S. PATENT DOCUMENTS

| 4,263,286 A | 4/1981 | Nakajima et al. |
| 4,393,863 A | 7/1983 | Osterholm |

(List continued on next page.)

FOREIGN PATENT DOCUMENTS

| JP | 02102290 | * | 4/1990 |

OTHER PUBLICATIONS

Melby, James M., Miner, Lewis C., and Reed, Donal J., Effect of Acetazolamide and Furosemide on the Production and Composition of Cerebrospinal Fluid from the Cat Choroid Plexus, Can. Journal Physiol. Pharmacology, vol. 60, 1982.
Matsukawa, Motomi, Akizawa, Toshifumi, Ohigashi, Masaaki, Morris, Jennifer F., Butler, Jr., Vincent P., and Yoshioka, Masanori, A Novel Bufadienolide, Marinosin, in the Skin of the Giant Toad, Bufo marinus, Chem. Pharm. Bull, vol. 45 No. 2, Feb. 1997.
McCarthy, Ken D. and Reed, Donal J., The Effect of Acetazolamide and Furosemide on Cerebrospinal Fluid Production and Choroid Plexus Carbonic Anhydrase Activity, The Journal of Phamacology and Experimental Therapeutics, vol. 189, No. 1, 1974.
Plangger, C. and Volkl, H, Effect of Furosemide, Bumetanide and Mannitol on Intracranial Pressure in Experimental Brain Edema of the Rat, Zent. bl. Neurochir. 50, 1989.
Greene, Jr., CI.S., Lorenzo, A.V., Hornig, G., and Welch, K., The Lowering of Cerebral Spinal Fluid and Brain Interstitial Pressure of Preterm and Term Rabbits by Furosemide, Z Kinderchir 40, Supplement I, 1985.
Bass, Norman H., Fallstrom, S.P., and Lundborg, Per, Digoxin–induced Arrest of the Cerebrospinal Fluid Circulation in the Infant Rat: Implications for Medical Treatment of Hydrocephalus During Early Postnatal Life, Pediat. Res., vol. 13, 1979.
Numazawa, Inoue, Naonori, Nakura, Hironori, Sugiyama, Tadashi, Fujino, Emi, Shinoki, Masa–Aki, Yoshida, Takemi, and Kuroiwa, Yukio, A Cardiotonic Steroid Bufalin–Induced Differentiation of THP–1 Cells, Biochemical Pharmacology, vol. 52, 1996.
McGowan, Michelle H., Russell, Paul, Carper, Deborah A., and Lichtsein, David, Na+, K+–ATPase Inhibitors Down–Regulate Gene Expression of the Intracellular Signaling Protein 14–3–3 in Rat Lens, The Journal of Pharmacology and Experimental Therapeutics, vol. 289, No. 3, 1999.
Halperin, Jose A., Digitalis–like Properties of an Inhibitor of the Na+/K+ Pump in Human Cerebrospinal Fluid, Journal of the Neurological Sciences, vol. 90, 1989.
Zivin, M.D., Ph.D., Justin A. and Degirolami, Umberto, M.D., Spinal Cord Infarction: A Highly Reproducible Stroke Model, Stroke, vol. 11, No. 2, 1980.
Pomfy, M. and Franko, J., Validation of a Four–Vessel Occlusion Model for Transient Global Cerebral Ischemia in Dogs, Journal of Brain Research, vol. 39, 1994.
Bircher, M.D., Nicholas and Safar, M.D., Peter, Cerebral Preservation During Cardiopulmonary Resuscitation, Critical Care Medicine, vol. 13, No. 3, 1985.
Little, M.D., John R. and O'Shaughnessy, M.Sc., Donald, Treatment of Acute Focal Ischemia with Continuous CSF Drainage and Mannitol, Stroke, vol. 10, No. 4, 1979.
Miyamoto, Kiyoshi, Ueno, Akira, Wada, Tatsuo, and Kimoto, Seiji, A New and Simple Method of Preventing Spinal Cord Damage Following Temporary Occlusion of the Thoracic Aorta by Draining the Cerebrospinal Fluid, 1959.
Wan, Innes Y.P., Angelini, Gianni D., Bryan, Alan J., Ryder, Ian, and Underwood, Malcolm J. Prevention of Spinal Cord Ischaemia During Descending Thoracic and Thoracoabdominal Aortic Surgery, European Journal of Cardio–thoracic Surgery, vol. 19, 2001.
Blaisdell, M.D., F. William and Cooley, M.D., Denton A., The Mechanism of Paraplegia After Temporary Thoracic Aortic Occlusion and its Relationship to Spinal Fluid Pressure, Surgery, Mar. 1962.

(List continued on next page.)

*Primary Examiner*—Jean C. Witz
(74) *Attorney, Agent, or Firm*—Cesari and McKenna, LLP

(57) ABSTRACT

After interruption of blood supply to central nervous system tissue, cerebral edema sets in. It has been shown that restoring blood flow to injured areas of the central nervous system after the onset of edema does not result in blood reperfusing the tissue. A composition and method for treating injured central nervous tissue, or preventing injury to central nervous system tissue is provided. The composition is generally an amphipathic lipid in an oil solution. The method provides for withdrawing cerebrospinal fluid from the subarachnoid spaces around the tissue to be treated or protected, and replacing that fluid with an approximately equivalent volume of the amphipathic lipid in oil composition. The treatment can be augmented with agents that suppress production of cerebrospinal fluid, or with other known agents.

15 Claims, No Drawings

U.S. PATENT DOCUMENTS

| | | | |
|---|---|---|---|
| 4,445,500 A | 5/1984 | Osterholm | |
| 4,445,887 A | 5/1984 | Osterholm | |
| 4,465,850 A | 8/1984 | Cragoe, Jr. et al. | |
| 4,758,431 A | 7/1988 | Osterholm | |
| 4,780,456 A | * 10/1988 | Pistolesi | 514/78 |
| 4,830,849 A | 5/1989 | Osterholm | |
| 5,085,630 A | 2/1992 | Osterholm et al. | |
| 5,089,515 A | 2/1992 | Morinaka et al. | |
| 5,128,354 A | 7/1992 | Masuda et al. | |
| 5,308,832 A | 5/1994 | Garleb et al. | |
| 5,395,314 A | 3/1995 | Klatz et al. | |
| 5,486,530 A | 1/1996 | Boelke et al. | |
| 5,755,237 A | 5/1998 | Rodriguez | |
| 5,879,677 A | 3/1999 | del Zoppo | |
| 6,123,956 A | 9/2000 | Baker et al. | |

OTHER PUBLICATIONS

Symbas, M.D., P.N., Pfaender, L.M., Drucker, M.D., M.H., Lester, M.D., J.L., Gravanis, M.D., M.B., and Zacharopoulos, M.D., L., Cross–clamping of the Descending Aorta, Hemodynamic and Neurohumoral Effects, J. Thorac Cardiovasc. Surg., vol. 85, 1983.

Wadouh, M.D., Faysal, Lindemann, D.D.M., Eva–Maria, Arndt, Christoph F., Hetzer, M.D., Roland, and Borst, M.D., Hans G., The Arteria Radicularis Magna Anterior as a Decisive Factor Influencing Spinal Cord Damage During Aortic Occlusion, J. Thorac Cardiovasc. Surg., vol. 88, 1984.

McCullough, M.D., James L., Hollier, M.D., Larry H., and Nugent, M.D., Michael Nugent, Paraplegia After Thoracic Aortic Occlusion: Influence of Cerebrospinal Fluid Drainage, Journal of Vascular Surgery, vol. 7, 1988.

Bower, M.D., Thomas C., Murray, M.D., Ph.D., Michael J., Gloviczki, M.D., Peter, Yaksh, Ph.D., Tony L., Hollier, M.D., Larry H., and Pairolero, M.D., Peter C., Effects of Thoracic Aortic Occlusion and Cerebrospinal Fluid Drainage on Regional Spinal Cord Blood Flow in Dogs: Correlation with Neurologic Outcome, Journal of Vascular Surgery, vol. 9, 1988.

Crawford, M.D., E. Stanley, Svensson, M.B., Ph.D., Lars G., Hess, MS, Kenneth R., Shenaq, M.D., Salwa S., Coselli, M.D., Joseph S., Safi, M.D., Hazim, Mohindra, M.D., Prita K., and Rivera, M.D., Victor, A Prospective Randomized Sutdy of Cerebrospinal Fluid Drainage to Prevent Paraplegia After High–Risk Surgery on the Thoracoabdominal Aorta, Journal of Vascular Surgery, vol. 13, 1990.

Azizzadeh, M.D., Ali, Huynh, M.D., Tam T.T., Miller, III, Ph.D., Chrales C., and Safi, M.D., Hazim, Reversal of Twice–Delayed Neurologic Deficits with Cerebrospinal Fluid Drainage After Thoracoabdominal Aneurysm Repair: A Case Report and Plea for a National Database Collection, Journal of Vascular Surgery, vol. 31, 2000.

Mauney, M.D., Michael C., Blackbourne, M.D., Lorne H., Laugenburg, M.D., Scott E., Buchanan, M.D., Scott A., Kron, M.D., Irving L., and Tribble, M.D., Curtis G., Prevention of Spinal Cord Injury After Repair of the Thoracic or Thoracoabdominal Aorta, Ann Thorac Surg., vol. 59, 1995.

Spence, M.D., Pual A., Lust, Ph.D., Robert M., Iida, M.D., Hiroshi, Sun, M.D., You Su, Austin III, M.D., Erle H., and Chitwood, Jr., M.D., W. Randolph, Reappraisal of the Mechanism for Cerebrospinal Fluid Hypertension During Aortic Surgery, Circulation, vol. 82, Supplement IV, 1990.

Chapman, M.D., Kristine M., Woolfenden, M.D., Andrew R., Graeb, M.D., Douglas, Johnston, M.D., Dean C.C., Beckman, M.D., Jeff, Schulzer, Ph.D., Michael, and Teal, M.D., Phil A., Intravenous Tissue Plasminogen Activator for Acute Ischemic Stroke, A Canadian Hospital's Experience, Stroke, vol. 31, 2000.

Kunihara, M.D., Takashi, Sasaki, M.D., Shigeyuki, Shiiya, M.D., Norihiko, Miyatake, M.D., Tsukasa, Mafune, Ph.D., Naoki, and Yasuda, M.D., Keishu, Proinflammatory Cytokines in Cerebrospinal Fluid in Repair of Thoracoabdominal Aorta, Ann. Thorac. Surg., vol. 71, 2001.

Effect of Intravenous Recombinant Tissue Plasminogen Activator on Ischemic Stroke Lesion Size Measured by Computed Tomography, Stroke, vol. 31, 2000.

Lapchak, Ph.D., Paul A., Chapman, MSC., Deborah F., Zivin, M.D., Ph.D., Justin A., Metalloproteinase Inhibition Reduces Thrombolytic (Tissue Plasminogen Activator)—Induced Hemorrhage After Thromboembolic Stroke, Stroke, vol. 31, 2000.

Forsting, M.D., Michael, Reith, M.D., Wolfgang, Schabitz, M.D., Wolf–Rudiger, Heiland, Ph.D., Sabine, Kummer, M.D., Rudiger Von, Hacke, M.D., Werner, Sartor, M.D., Klaus, Decompressive Craniectomy for Cerebral Infarction, An Experimental Study in Rats, Stroke, vol. 26, No. 2, Feb. 1995.

Engelhorn, M.D., Tobias, Doerfler, M.D., Arnd, Kastrup, M.D., Andreas, Beaulieu, Ph.D., Christian, De Crespigny, Ph.D., Alexander, Forsting, M.D., Michael, and Moseley, Ph.D., Michael E., Decompressive Craniectomy, Reperfusion, or a Combination for Early Treatment of Acute "Malignant" Cerebral Hemispheric Stroke in Rats? Potential Mechanisms Studied by MRI, Stroke, vol. 30, 1999.

Osterholm, M.D., Jewell L., Alderman, Ph.D., John B., Triolo, Ph.D., Anthony, D'Amore, B.S., Bendedette R., and Williams, M.T., Hyacinth D., Oxygenated Fluorocarbon Nutrient Solution in the Treatment of Experimental Spinal Cord Injury, Neurosurgery, vol. 15, 1984.

Osterholm, M.D., Jewell L., Alderman, Ph.D., John B., Triolo, Ph.D., Anthony J., D'Amore, B.S., Benedette R., Williams, M.T., Hyacinth D., and Frazer, B.S., Glen, Severe Cerebral Ischemia Treatment by Ventriculosubarachnoid Perfusion with an Oxygenated Fluorocarbon Emulsion, Neuosurgery, vol. 13, 1983.

Sklar, M.D., Fredrick H. and Long, M.D., Donlin M., Recirculatory Spinal Subarachnoid Perfusions in Dogs: A Method for Determing CSF Dynamics Under Non–Steady State Conditions, Neurosurgery, vol. 1, No. 1, 1977.

Fujimoto, M.D., Shunichi, Mizoi, M.D., Kazuo, Yoshimoto, M.D., Takashi, and Suzuki, M.D., Jiro, The Protective Effect of Vitamin E on Cerebral Ischemia, Surg. Neurol., vol. 22, 1984.

Sacco, M.D., Ralph L., Derosa, Janet T., Haley, Jr., M.D., E. Clarke, Levin, Ph.D., Bruce, Ordronneau, Ph.D., Paul, Phillips, Stephen J., Rundek, M.D., Ph.D., Tanja, Snipes, M.D., Rose G., Thompson, Ph.D., John L., Glycine Antagonist in Neuroprotection for Patients with Acute Stroke, JAMA, vol. 285, No. 13, Apr. 4, 2001.

Rossberg, M.D., Mark I., Murphy, Ph.D., Stephanie J., Traystman, Ph.D., Richard J., and Hurn, Ph.D., Patricia D., LY3533811.HCl, A Selective Estrogen Receptor Modulator, and Experimental Stroke, Stroke, vol. 31, 2000.

Sterz, M.D., Fritz, Leonov, M.D., Yuval, Safar, M.D., Peter, Radovsky, Ph.D, Ann, Stezoski, S. William, Reich, M.D., Harvey, Shearman, Ph.D., Gary, and Greber, Terrence F., Effect of Excitatory Amino Acid Receptor Blocker MK–801 on Overall, Neurologic, and Morphologic Outcome after Prolonged Cardiac Arrest in Dogs, Anesthesiology, vol. 71, 1989.

Schielke, Ph.D., Gerald P., Kupina, Nancy C., Boxer, Ph.D., Peter A., Bigge, Ph.D., Christopher F., Welty, Ph.D., Devin, The Neuroprotective Effect of the Novel AMPA Receptor Antagonist PD 152247 (PNQX) in Temporary Focal Ischemia in the Rat, Stroke, vol. 30, 1999.

Ames III, M.D., Adelbert, Wright, M.D., Lewis, Kowada, M.D., Masayoshi, Thurston, Jean M., and Majno, M.D., Guido, The No–Reflow Phenomenon, Cerebral Ishcemia, vol. 52, No. 2, Feb. 1968.

Chiang, M.D., Jose, Kowada, M.D., Masayoshi, Ames III, M.D., Adelbert, Wright, M.D., R. Lewis, and Majno, M.D., Guido, Vascular Changes, Cerebral Ischemia, vol. 52, No. 2, Feb. 1968.

Mackert, B.M., Staub, F., Peters, J., Baethmann, A., and Kempski, O., Anoxia in Vitro Does Not Induce Neuronal Swelling or Death, Journal of the Neurological Sciences, vol. 139, 1996.

Ames III, A. and Gurian, B.S., Effects of Glucose and Oxygen Deprivation on Function of Isolated Mammalian Retina, Office of Scientific Research, vol. 49, 1962.

McManis, Phillip G., Schmelzer, James D., Zollman, Paula J., and Low, Phillip A., Blood Flow and Autoregulation in Somatic and Autonomic Ganglia: Comparison with Sciatic Nerve, Brain, vol. 120, 1997.

Korthals, Jan K., Maki, Toshiyuki, and Gieron, Maria A., Nerve and Muscle Vulnerability to Ischemia, Journal of the Neurological Sciences, vol. 71, 1985.

Hossmann, Konstantin–Alexander, Reperfusion of the Brain After Global Ischemia: Hemodynamic Disturbances, Shock, vol. 8, No., 2, 1997.

Bentley, F.H. and Schlapp, W., Experiments on the Blood Supply of Nerves, J. Physiol., vol. 102, 1943.

Schmelzer, J.D., Zochodne, D.W., and Low, P.A., Ischemic and Reperfusion Injury of Rat Peripheral Nerve, Proc. Natl. Acad. Sci., vol. 86, 1989.

Nagamatsu, M.D., Masaaki, Schmelzer, James D., Zollman, Paula J., Smithson, Inge L., Nickander, Kim, K., and Low, M.D., Phillip A., Ischemic Reperfusion Causes Lipid Peroxidation and Fiber Degeneration, Muscle and Nerve, vol. 19, Jan. 1996.

Simon, R.P., Swan, J.H., Griffiths, T., and Meldrum, B.S., Blockade of N–Methyl–D–Aspartate Receptors May Protect Against Ischemic Damage in the Brain, Science, vol. 226, May 1984.

Flamm, M.D., Eugene S., Demopoulos, M.D., Harry B., Seligman, Ph.D., Myron, Poser, Richard G., and Ransohoff, M.D., Joseph, Free Radicals in Cerebral Ischemia, Stroke, vol. 9, No. 5, Sep.–Oct. 1977.

Coyle, Joseph T. and Puttfarcken, Pamela, Oxidative Stress, Glutamate, and Neurodegenerative Disorders, Science, vol. 262, Oct. 29, 1993.

Rothman, M.D., Steven M. and Olney, M.D., John W., Glutamate and the Pathophysiology of Hypoxic–Ischemic Brain Damage, Annals of Neurology, vol. 19, No. 2, Feb. 1986.

Plum, M.D., Fred, Neuroprotection in Acute Ishemic Stroke, JAMA, vol. 285, No. 13, Apr. 4, 2001.

Hickenbottom, M.D., Susan L. and Grotta, M.D., James, Neuroprotective Theraphy, Seminars in Neurology, vol. 18, No. 4, 1998.

Dirnagl, Ulrich, Iadecola, Constantino, and Moskowitz, Michael A., Pathobiology of Ischaemic Stroke: An Integrated View, TINS, vol. 22, No. 9, 1999.

Fisher, M.D., Marc and Schaebitz, M.D., Wolf, An Overview of Acute Stroke Therapy, Arch. Intern. Med., vol. 160, Nov. 27, 2000.

Jonas, A., Ayigari, V., Viera, D., and Waterman, P., Neuroprotection Against Cerebral Ischemia: A Review of Animal Studies and Correlation with Human Trial Results, Neuroprotective Agents, vol. 890, 1999.

Chua, H.C. and Ng, P.Y., Neuroprotection in Acute Stroke, vol. 30, No. 2, Mar. 2001.

Nagahiro, Shinji, Uno, Masaaki, Koichi, Sato, Goto, Satoshi, Morioka, Motohiro, and Ushio, Yukitaka, Pathophysiology and Treatment of Cerebral Ischemia, The Journal of Medical Investigation, vol. 45, 1998.

Del Zoppo, Gregory, Ginis, Irene, Hallenbeck, John M., Iadecola, Constantino, Wang, Xinkang, and Feuerstein, Giora Z., Inflammation and Stroke: Putative Role for Cytokines, Adhesion Molecules and iNOS in Brain Response to Ischemia, Brain Pathology, vol. 10, 2000.

Boyle, Jr., M.D., Edward M., Pohlman, M.D., Timothy H., Cornejo, M.D., Carol J., and Verrier, M.D., Edward D., Endothelial Cell Injury in Cardiovascular Surgery: Ischemia–Reperfusion, Ann. Thorac.. Surg., vol. 62, 1996.

Faden, Alan I. and Salzman, Steven, Pharmacological Strategies in CNS Trauma, TiPS, vol. 13, Jan. 1992.

Wada, M.D., Shoichi, Yone, M.D., Kazunori, Ishidou, M.D., Yasuhiro, Nagamine, M.D., Tomonori, Nakahara, M.D., Shinji, Niiyama, M.D., Takahito, and Sakou, M.D., Takashi, Apoptosis Following Spinal Cord Injury in Rats and Preventative Effect of N–Methyl–D–Aspartate Receptor Antagonist, Journal of Neurosurgery, vol. 91, Jul. 1999.

Nockels, Russ and Young, Wise, Pharmacologic Strategies in the Treatment of Experimental Spinal Cord Injury, Journal of Neurotrauma, vol. 9, 1992.

Sun, Feng–Yan and Faden, Alan I., High–and–Low–Affinity NMDA Receptor–Binding Sites in Rat Spinal Cord: Effects of Traumatic Injury, Brain Research, vol. 666, 1994.

Yaksh, Tony L., Hua, Xiao–Ying, Kalcheva, Iveta, Nozaki–Tagauchi, Natsuko, and Marsala, Martin, The Spinal Biology in Humans and Animals of Pain States Generated by Persistent Small Afferent Input, Proc. Natl. Acad. Sci., vol. 96, 1999.

Agrawal, Sandeep K. and Fehlings, Michael G., Role of NMDA and Non–NMDA Ionotropic Glutamate Receptors in Traumatic Spinal Cord Axonal Injury, The Journal of Neuroscience, vol. 17, Feb. 1, 1997.

Yanase, M.D., Mitsuhiro, Sakou, M.D., Takashi, and Fukuda, M.D., Takeo, Role of N–Methyl–D–Aspartate Receptor in Acute Spinal Cord Injury, Journal of Neurosurgery, vol. 83, Nov. 1995.

Liu, Shanliang, Ruenes, Gladys L., and Yezierski, Robert P., NMDA and Non–NMDA Receptor Antagonists Protect Against Excitotoxic Injury in the Rat Spinal Cord, Brain Research, vol. 756, 1997.

Liu, Ph.D., Yuanbin, Rosenthal, M.D., Rosenthal, Haywood, M.D., Yolanda, Miljkoviclolic, M.D., Milena, Vanderhoek, Ph.D., Jack Y., and Fiskum, Ph.D., Gary, Normoxic Ventilation After Cardiac Arrest Reduces Oxidation of Brain Lipids and Improves Neurological Outcome, Stroke, vol. 29, 1998.

Zager, M.D., Eric L. and Ames III, M.D., Adelbert, Reduction of Cellurlar Energy Requirements: Screening for Agents That May Protect Against CNS Ischemia, Journal of Neurosurgery, vol. 69, Oct. 1988.

Gorelick, Philip B., Neuroprotection in Acute Ischaemic Stroke: A Tale of for Whom the Bell Tolls, The Lancet, vol. 355, Jun. 3, 2000.

Lees, Kennedy R., Asplund, Kjell, Carolei, Antonio, Davis, Stephen M., Diener, Hans–Christoph, Kaste, Markku, Orgogozo, Jean–Marc, and Whitehead, John, Glycine Antagonist (Gavestinel) in Neuroprotection (GAIN International) in Patients with Acute Stroke: A Randomised Controlled Trial, The Lancet, vol. 355, Jun. 3, 2000.

Degraba, M.D., Thomas J. and Pettigrew, M.D., Creed, Why Do Neuroprotective Drugs Work in Animals But Not in Humans?, Stroke, vol. 19, No. 2, May 2000.

De Keyser, Jacques, Sulter, Geert, and Luiten, Paul G., Clinical Trials With Neuroprotective Drugs in Acute Ischaemic Stroke: Are we Doing the Right Thing?, TINS, vol. 22, No. 12, 1999.

De Keyser, Jacques, Sulter, Geert, and Luiten, Paul G., Clinical Trials With Neuroprotective Drugs in Acute Ischaemic Stroke: Are we Doing the Right Thing?, TINS, vol. 23, No. 6, 2000.

Thrombolytics, www.stroke.org., National Stroke Association, Accessed on Aug. 21, 2001.

Neuron Therapeutics, Inc., www.neurontherapeutics.com, Accessed on Aug. 21, 2001.

Department of Neurology, www.jerffersonhospital.org, Accessed on Aug. 21, 2001.

The Internet Stroke Center, www.neuro.wustl.edu/stroke/therapy/TherapyIndex1, Stroke Investigational Therapy, Accessed on Dec. 8, 1999

The Internet Stroke Center, www.neuro.wustl.edu/stroke/trials/TrialList1, Clinical Trials Database, Accessed on Dec. 8, 1999.

Stroke Research Summary, www.stroke.org, Stroke Research Summary for Professionals Only, Accessed on Dec. 8, 1999.

Plestis, M.D., K.A., Nair, M.D., D.G., Russo, M., and Gold, M.D., J.P., Left Atrial Femoral Bypass and Cerebrospinal Fluid Drainage Decreases Neurologic Complications in Repair of Descending and Thoracoabdominal Aortic Aneurysms, Annals of Vascular Surgery, vol. 15, 2001.

Database Derwent Acc No.: 1990–160455. Soluble tocopherol compsn.—contains tocopherol, sugar, and lecithin. JP 02102290A (Nippon Oils & Fats Co.) Apr. 13, 1990.

* cited by examiner

COMPOSITION AND TREATMENT METHOD FOR BRAIN AND SPINAL CORD INJURIES

BACKGROUND OF THE INVENTION

1. Field of the Invention

This invention is related to medical formulations used to treat and protect the central nervous system and methods of using those formulations. In particular, the invention relates to neuroprotective compositions and methods using those compositions to protect the brain or minimize lasting damage.

2. Background Information

Most Central Nervous System (CNS) injuries, including stroke, trauma, hypoxia-ischemia, multiple sclerosis, seizure, infection, and poisoning directly or indirectly involve a disruption of blood supply to the CNS, and share the same common pathologic process, that is: rapid cerebral edema leading to irreversible brain damage, and eventually to brain cell death.

One common injury to the CNS is stroke, the destruction of brain tissue as a result of intracerebral hemorrhage or infarction. Stroke is a leading cause of death in the developed world. It may be caused by reduced blood flow or ischemia that results in deficient blood supply and death of tissues in one area of the brain (infarction). Causes of ischemic strokes include blood clots that form in the blood vessels in the brain (thrombus) and blood clots or pieces of atherosclerotic plaque or other material that travel to the brain from another location (emboli). Bleeding (hemorrhage) within the brain may also cause symptoms that mimic stroke.

CNS tissue is highly dependent on blood supply and is very vulnerable to interruption of blood supply. Without neuroprotection, even a brief interruption to the blood flow to the central nervous system can cause neurologic deficit. The brain is believed to tolerate complete interruption of blood flow for a maximum of about 5 to 10 minutes.

It has been observed that after blood flow is restored to areas of the brain that have suffered an ischemic injury, secondary hemodynamic disturbances have long lasting effects that interfere with the ability of the blood to supply oxygen to central nervous system tissues. This has been called the "no-reflow" phenomenon.

Similarly, interruption of the blood flow to the spinal cord, for even short periods of time, can result in the "no-reflow" phenomenon leading to paralysis.

Recognition of the "ischemic penumbra," a region of reduced cerebral blood flow in which cell death might be prevented, has focused attention on treatments that might minimize or reverse brain damage when administered soon after stroke onset. Enlargement of infarct volume is determined by changes in metabolism caused by initiation of the ischemic cascade. This cascade involves energy supply failure, membrane depolarization, release of neurotransmitters (including glutamate in large amounts), accumulation of intracellular calcium, increased production of nitric oxide and free radicals, development of cellular edema, and finally, cell death. Each step along the ischemic cascade offers a potential target for therapeutic intervention. To date, several classes of neuroprotective compounds have been investigated in phase 3 trials for acute stroke. They have included calcium channel antagonists, N-methyl-D-aspartate (NMDA) receptor antagonists, free radical scavengers, anti-intercellular adhesion molecule 1 antibody, GM-1 ganglioside, [gamma]-aminobutyric acid agonists, and sodium channel antagonists, among others. All of the trials have yielded disappointing efficacy results and some showed safety problems, including increased mortality or psychotic effects, which resulted in their early termination.

A neuroprotectant is a substance that can increase the tolerance of CNS tissues to injury or disruption of blood supply. A broad spectrum of compounds with disparate mechanisms of action have been considered, from oxygen free radical scavengers, calcium channel blockers and glutamate receptor antagonists to monoclonal antibodies that attempt to curtail inflammatory cascades occurring in cerebral injuries. Although several of these agents seems have been effective in vitro, very few have shown real advantages in in vivo testing or clinical studies. These agents are directed to molecular mechanisms of nerve cell injuries, but they do not address the one injury path common to all CNS injuries, cerebral edema.

Current treatments for stroke include recombinant tissue plasminogen activator (rt-PA), a thrombolytic agent, that has been shown to be effective dissolving clots to restore blood flow to injured areas of the brain if used within 3 hours after the onset of the stroke.

U.S. Pat. No. 5,755,237 to Rodriguez discloses acetazolamide for the treatment of brain edema. Acetazolamide can inhibit cerebrospinal fluid production, but administering of acetazolamide alone does not have a neuroprotective effect.

A series of patents, U.S. Pat. Nos. 4,981,691, 4,758,431, 4,445,887, 4,445,500, and 4,393,863 to Osterholm disclose a fluorocarbon solution for treatment of hypoxic-ischemic neurologic tissue.

SUMMARY OF THE INVENTION

Many proposed neuroprotective agents such as oxygen free radical scavengers, NMDA receptor antagonists, and apoptosis inhibitors seem to have measurable effect in vitro. However, during in vivo study and clinical trials, these agents do not show a neuroprotective effect.

I have now found that draining the cerebrospinal fluid (CSF) from the central nervous system, and replacing the CSF with an oil combined with an amphipathic lipid to adsorb edematous liquid in the CNS prevents cerebral edema. Elimination of this cerebral edema prevents the onset of the no-reflow phenomenon, enabling blood to reperfuse CNS tissue after significant periods of ischemia. Preventing the continuing hemodynamic disturbance, the no-reflow phenomenon, protects the CNS tissue making it resistant to injuries, and lengthening the therapeutic window for all other therapies.

This invention provides compositions and methods for protecting brain and spinal cord from injuries resulting from interruption of blood flow. Compositions according to this invention may be used to treat neurological disorders, such as stroke, hypoxia-ischemia, hemorrhage, trauma, multiple sclerosis, seizure, infection, or poisoning. The compositions are also useful during open-heart surgery, neurosurgery, shock, or other procedures where blood flow to the CNS is interrupted.

There are many advantages to the compositions and method I have discovered.

One advantage is improving the efficacy of existing treatments for stroke, head trauma, and other invasive procedures. Administering an effective neuroprotectant agent according to this invention will increase the therapeutic window, the period of time in which any other treatment, including thrombolytic agents can be used. For example, tPA, the only FDA approved medication for stroke, is a thrombolytic agent targeted on dissolving the blood clots that led to the stroke. tPA is not targeted on, and has no observed effect on cerebral edema. tPA is now only approved for use within 3 hours after onset of ischemia. When used in combination with the instant composition and method, the therapeutic window for all known treatments now used for supporting CNS tissue will be much longer.

This invention, if combined with other known techniques such as controlled hypothermia, may significantly increase the length of time a patient can tolerate cerebral ischemia. A patient treated according to this invention may survive invasive procedures performed on any part of the CNS without injury, including areas of the brain that have not been surgically accessible prior to this invention. Additionally, procedures that require interruption of the blood flow, such as heart surgery, repair of aortic aneurysm, or any other surgery where systemic blood circulation is interrupted can be performed with increased safety.

The compositions and methods I have invented extend the therapeutic window for successfully recovering from a stroke or cardiac arrest from mere minutes to hours. In addition, this compositions and method are useful for screening neuroprotective agents developed based on other mechanisms.

The formulations I have found that have a neuroprotective effect are organic solutions. These solutions include an amphipathic lipid in an oil. Optionally, the treatment solution may include one of more of the following: an osmotic dehydrant; a compound that may supply energy to a cell; a compound that decreases the metabolism of the cell; or an agent that suppresses the production of cerebrospinal fluid.

I have found the formulations I have used are effective when it is applied to the subarachnoid spaces after the cerebrospinal fluid has been removed from the subarachnoid spaces. These methods are effective to treat injured central nervous system tissue or to protect that tissue from continuing damage after injury of trauma.

The compositions and methods are effective to treat stroke.

The compositions and methods enhance the effectiveness of neuroprotective agents.

The compositions and methods can extend to the therapeutic window of thrombolytic agents such as recombinant tissue plasminogen activator.

DETAILED DESCRIPTION OF AN ILLUSTRATIVE EMBODIMENT

In ischemic injury, CSF has a toxic effect facilitating cerebral edema, blocking cerebral blood flow and collateral circulation to damaged nerve tissue, the no-reflow phenomenon. This failure of circulation results in continuing damage to CNS tissue after the interruption of blood flow is reversed. Restoration of blood flow to the affected area of the CNS after a period of ischemia as short as six minutes does not result in blood re-flow to the affected CNS tissue. After blood flow to the CNS is interrupted, CSF infiltrates the CNS tissue causing edema. The edematous CSF remains in the CNS tissue preventing blood re-flow into the affected tissues after blood circulation is restored. As the duration of blood flow interruption increases, the edema spreads throughout the CNS tissue causing additional damage in an ischemic cascade.

In the adult human, the average intra-cranial volume is about 1700 ml. The volume of the brain is approximately 1400 ml; CSF volume ranges from about 52 to about 160 ml (mean 140 ml), and blood volume is about 150 ml. Thus, the CSF occupies about 10 percent of the intra-cranial and intra-spinal volume.

The choroid plexuses are the main sites of CSF formation. The average rate of CSF formation is about 21 to 22 ml/hr, or approximately 500 ml/day. The CSF as a whole is renewed four or five times daily. CSF formation is related to intracranial pressure. When the intracranial pressure is below about 70 mm $H_2O$, CSF is not absorbed, and production increases. CSF is a very dilute aqueous solution with a low colloidal osmotic pressure.

The CSF has a mechanical function. It serves as a kind of water jacket for the spinal cord and brain, protecting them from trauma and acute changes in venous blood pressure. The CSF provides buoyancy and shock absorption, so that brain and spinal cord float in a CSF pool. CSF does not appear to be necessary to brain or spinal cord metabolism. However, during ischemic episodes, CFS has a toxic effect by facilitating cerebral edema and the resulting in no-reflow phenomenon after disruption of blood flow to CNS tissue.

The mechanism of injury leading to brain edema is not fully understood. However, when the blood flow to the nerve cells has been interrupted, there is a shift of electrolytes and fluids across the nerve cell membranes. Swelling (edema) occurs when the CNS tissue absorbs fluid such as CSF. When injury occurs, CSF readily penetrates CNS tissues. Additionally the edema may cause collapse of blood vessels within the affected tissue. Ischemic injury to the central nervous system may be either global, in the case of general failure of blood circulation after a cardiac arrest, or local over an area of any size after for example, a head trauma, an intra-cerebral hemorrhage, or a stroke. It is known however, that if cerebral edema induced by ischemia of whatever dimension is not controlled, then the edema spreads and the severity of the resultant injury rapidly increases.

In order to prevent cerebral edema, and the irreversible effects that occur after ischemia, the CSF is withdrawn from the affected area of the CNS. It is preferred to completely remove all CSF from the injured area. It is advantageous to completely remove all CSF from the CNS. However, it is very difficult, almost impossible, mechanically to remove CSF completely from the subarachnoid spaces or the brain surface because the brain contour is very complex with many sulci, gyri and pools. Even if the intra cranial pressure is mechanically reduced below zero, surface tension and capillary forces retain CSF in the spaces between the dura and the cerebral surface. Similarly, in edematous cerebral tissue, CSF is retained in Virchow-Robin space (or extra cellular space), including the spaces surrounding smaller vessels that penetrate into the brain from the periphery.

Mechanically withdrawing CSF alone is not sufficient to achieve the neuroprotective effect. This residual aqueous CSF can significantly decrease the protective effect because it is a continued source of edematous fluid that can cause delayed or recurring injury. Removing CSF from the edematous tissue is necessary to prevent the occurrence of the no-reflow phenomenon. CSF remaining in the area of edema exerts pressure on blood vessels in the area, preventing blood flow from reaching the affected CNS tissues even after blood flow is restored.

In this method, the CSF is withdrawn from the cerebral circulation through one or more cannulas. For maximum CNS tissue protection, two small holes are drilled on the skull, the dura is punctured, and a cannula is placed in through the dura into the subarachnoid spaces. Additional cannulas may be inserted into the lateral cerebral ventricles, the lumbar theca, and the cisterna magna. CSF can be removed from any or all of these locations to remove edematous fluid, or to reduce and prevent edema.

For a spinal cord injury, a cannula may be placed through a puncture in the lumbar theca or cisterna magna. Optionally, two cannulas may be used.

CSF pressure control has been used for protecting spinal cord during aortic surgery. Controlling the pressure of CFS, in particular, maintaining a pressure lower than the central venous pressure can be advantageous in protecting the spinal cord from injury during aortic surgery. However, such pressure control does not achieve the neuroprotective effect in the case of more general ischemia. Removing CSF from the spinal cord's subarachnoid space is relatively easier (compared with from brain) because of spinal cord's more simple contour. However, simple withdrawal of CSF even under controlled conditions in thoraco-aortic surgery, is not predictably effective protecting CNS tissue.

Complete removal of CSF reduces or eliminates edema in the CNS, but removal alone is not sufficient to protect the CNS from damage. As discussed above, the CSF performs a support and shock absorbing function, accordingly some liquid medium is necessary to support the CNS tissues in the body. In addition to providing a support media for the CNS tissues, it is important to maintain a controlled level of pressure within the CNS. Carefully controlling the pressure is necessary to prevent severe headache, or further disruption of blood flow.

In the instant method, the CSF (usually 50–200 ml) is withdrawn from the cranium and spinal cord. As discussed above, it is advantageous to completely remove the CSF, but for a localized injury, or for a spinal cord injury, beneficial effects can be achieved upon removal of a lesser volume of CSF. If it is not possible to remove the CSF, from the injured site, the CSF may be displaced with a treatment oil.

After the CSF has been withdrawn, an equal volume of treatment oil is injected into the space surrounding the affected CNS. This treatment oil performs the mechanical functions of the CSF, i.e. insulating the brain tissue from shock and providing a media to support the CNS organs buoyantly. Because the volume of treatment inserted into the cranium or the spinal cord is approximately equal to the volume of the CSF withdrawn, the intercranial pressure is stabilized and hernia or hemorrhage are prevented. The treatment oil supports the CNS tissues. It also coats the surfaces of the CNS tissue forming a lipid barrier that inhibits the penetration of CSF into the CNS tissues. The surfaces of the CNS tissues have a greater affinity for the non-polar oil than for the aqueous CSF. Because the density of the treatment oil is less than that of CSF, rotating the body about an axis, or elevating the head, will allow the treatment oil to cover all CNS tissue surfaces.

The treatment oil is an organic solution including an amphipathic lipid in oil. Other ingredients may be added including agents to suppress production of CSF, or other therapeutic agents. The treatment oil has a density less than that of water, but sufficient to support the organs of the CNS buoyantly. The treatment oil should have a physiologic pH.

The oil can be any non-aqueous, liquid, low viscosity material that is soluble in organic solvents but immiscible with water. Hydrocarbon oils and silicone oils are effective. Soybean oil, cod liver oil, vitamin E oil, olive oil, canola oil, corn oil, mineral oil, and mixtures of these oils in any concentration ratio may be used. Oils containing high concentrations of omega-3 fatty acid oils such as fish oils or their mixtures can be used, and may be advantageous because of their anti oxidant properties. However, any stable, low viscosity, non-aqueous fluid can be used, including fluorocarbons such as the Fluorinert® compounds manufactured by 3M Company of St. Paul Minn.

While the oil alone can have significant effect, I have found that adding an amphipathic lipid to the oil compositions enhances the neuroprotective effect. The amphipathic lipid is generally any organic molecule having both a polar functional group, such as a carbonic acid, phosphate, or other polar functional group at one end, and a non-polar, hydrocarbon functional group at another end. Examples of the amphipathic agents used in this composition include fatty acids, phosphoglycerides, sphingomyelins, glycolipids, cholesterol, cholesterol hemisuccinate, sphingolipids, and cerebrosides. Surface active agents, such as, Triton X-100 and didodecyldimethylammonium bromide, may be also used. Lecithin, a phospholipid that is a constituent of cell membranes, has been shown to be effective. However, any amphipathic lipid added to the oil is effective.

To make the treatment oil, the amphipathic lipid is added in a concentration of from about 0.1 to about 40 grams to 100 ml of the oil. The concentration used is limited only by the solubility of the amphipathic lipid in the particular oil used. Concentrations of from about 0.1 to about 10 grams of amphipathic lipid per 100 ml of can be easily prepared. Concentrations of about 1 gram of amphipathic lipid per 100 ml of oil can be used for direct comparison of the relative effect of any amphipathic lipid in any particular oil.

Treatment oil with the amphipathic lipid draws edematous CSF fluids away from the CNS tissue and into the treatment oil. The amphipathic component of the composition acts as a hook to pull out the water from Virchow-Robin space in the edematous tissue. This reduces the extent of any existing edema and prevents the spread of the edema. Additionally, the treatment oil with amphipathic lipid compositions is effective reducing edema when administered after the onset of edema. The amphipathic lipid improves the efficacy of the treatment oil under most circumstances, particularly when administered some time after the onset of edema.

The effect of this treatment oil/amphipathic lipid composition can be achieved over a period of several hours. In some cases, a substantial period of time is required for withdrawal of edematous fluid from the cells in the injured area. In addition, it may take a substantial time for injured CNS tissue to recover. Because of the lengthy periods of time, recurrent and delayed CSF toxicity are a significant concern. Suppressing production of CSF during treatment can be advantageous.

There are many known agents that inhibit production of CSF. These include Furosemide (20–200 mg every 4–6 hours), and acetazolamide (0.25–2 g every 4–12 hours). Other agents known to suppress formation of CSF include: beta blocking agents such as isopranolol, and timolol maleate; and calcium channel blockers such as brinzolamide, dorzolamide, methazolamide, sezolamide, lantanoprost, and bis (carbonyl) amidothiadiazole sulfonamides; and carbonic acid anhydrase inhibitors such as triamterene, spironolactone, thiazides, and, Na and K-ATPase inhibitors. This CSF inhibiting agent can be administered intravenously or orally in cases where circulation to the brain has not been impaired, or by direct injection to subarachnoid space, either in combination with the treatment oil, or alone to inhibit new CSF production.

While these agents are known to lower CSF production, these agents alone do not have a neuroprotective effect in an ischemic incident. Lowering the intracranial pressure or stopping the CSF production without removing the edematous CSF from the subarachnoid spaces does not achieve a neuroprotective effect. The CSF in the cranial cavity at the time blood flow is interrupted is enough to cause the cerebral edema and tissue damage.

The compositions and methods herein can be advantageously combined with any of the compositions used to treat stroke or other neurological deficiencies including: calcium channel blockers such as Nimodipine, and Flunarizine; calcium chelators, such as DP-b99; potassium channel blockers; Free radical scavengers—Antioxidants such as Ebselen, porphyrin catalytic antioxidant manganese (III) meso-tetrakis (N-ethylpyridinium-2-yl) porphyrin, (MnTE-2-PyP (5+)), disodium 4-[(tert-butylimino) methyl] benzene-1,3-disulfonate N-oxide (NXY-059), N:-t-butyl-phenylnitrone or Tirilazad; GABA agonists including Clomethiazole; GABA receptor antagonists, glutamate antagonists, including AMPA antagonists such as GYKI 52466, NBQX, YM90K, YN872, ZK-200775 MPQX, Kainate antagonist SYM 2081, NMDA antagonists, including competitive NMDA antagonists such as CGS 19755 (Selfotel); NMDA channel blockers including Aptiganel (Cerestat), CP-101,606, Dextrorphan, destromethorphan, magnesium, metamine, MK-801, NPS 1506, and Remacemide; Glycine site antagonists including ACEA 1021, and GV 150026; polyamine site antagonists such as Eliprodil, and Ifenprodil; and adenosine receptor antagonists; Growth factors such as Fibroblast Growth Factor (bFGF), Glial cell line derived neurotrophic factor (GDNF), brain derived neurotrophic factor, insulin like growth factor, or neurotrophin; Leukocyte adhesion inhibitors such as Anti ICAM antibody (Enlimomab) and Hu23F2G; Nitric oxide inhibitors including Lubeluzole; opiod antagonists, such as Naloxone, Nalmefenem, Phosphatidyleholine precursor, Citicoline (CDP-coline); Serotonin agonists including Bay x 3072; Sodium channel blockers such as Fosphenytoin, Lubeluzole, and 619C89; Potassium channel openers such as BMS-204352; anti-inflamatory agents; protein kinase inhibitors, and other agents whose mechanism of action is unknown or uncertain including: Piracetam and albumin. Other active agents, that provide energy to cells, such as ATP, co-enzyme A, co-enzyme Q, or cytochrome C may be added. Similarly, agents known to reduce cellular demand for energy, such as phenytoin, barbital, or lithium may be added to the oil.

The compositions and methods can be combined with and enhance the efficiency of thrombolytic agents such as: recombinant tissue plasminogen activator (rtpA), streptokinase, and tenecteplase in dissolving thrombosis in management of stroke or myocardial infarction.

Osmotic dehydrants, such as mannitol, sorbitol, or glycerin may assist in removal of CSF from edenateous tissue.

EXAMPLE ONE
Treatment for Spinal Cord Ischemia

The acute spinal cord ischemia was induced in twenty-nine rabbits. Group one: 8 rabbits for Soybean oil treatment. Group two: 9 rabbits for Vitamin E injection solution (1 mg/ml) treatment. Group three: 12 rabbits for control.

Halothane was given for anesthesia. A cannula was surgically positioned in the cistema magna in each rabbit. An abdominal incision was made and the aorta was isolated at the level of the renal artery. The aorta was cross-clamped by a clip just caudal to the left (lower) renal artery for one hour to produce spinal cord ischemic injury, then the clip was removed to resume blood supply.

For group one, at 5 minutes after ischemia, 0.8–1.2 ml CSF was withdrawn from the cisterna magna, then same amount of Soybean oil was administered through the cannula. Meanwhile, 40 mg furosemide was administered intravenously.

For group two, at 5 minutes after ischemia, 0.8–1.2 ml CSF was withdrawn from the cisterna magna, then same amount of Vitamin E injection solution was administered through the cannula. Meanwhile, 40 mg furosemide was administered intravenously.

For group three, at 5 minutes after ischemia, 0.8–1.2 ml CSF was withdrawn from the cistema magna, then same amount of saline (0.8–1.2 ml) is administered through the cannula. Meanwhile, 1 ml of normal saline was administered intravenously.

At 24 hours and one week after ischemic injury, the rabbits were tested for behavioral deficit (grade 0: complete recovery; grade 1: able to stand, but unable to walk normally; grade 2: good movement of the hind limbs, but unable to stand; grade 3: spastic paraplegia with slight movement of the hind limbs; grade 4: spastic paraplegia with no movement to the hind limbs).

The result is summarized as following: At both 24 hours and one week after ischemia, in group one and group two, all rabbits showed no behavioral deficit (grade 0), all walked and moved smoothly. In group three, all of rabbits showed complete spastic paraplegia with no movement to the hind limbs (grade 4).

EXAMPLE TWO
Delayed Treatment for Spinal Cord Ischemia

Acute spinal cord ischemia was induced in nine rabbits according to the method in Example One. Group one: 5 rabbits for 1% Lecithin Soybean oil 1 gram lecithin dissolved in 100 ml Soybean oil solution). Group two: 2 rabbits for Soybean oil solution. Group three: 2 rabbits for simple CSF withdrawal.

In group one, at 30 minutes after ischemia, 0.8–1.2 ml CSF was withdrawn from the cistema magna, then same amount of 1% Lecithin Soybean oil solution was administered through the cannula. Meanwhile, 40 mg furosemide was administered intravenously.

In group two, at 30 minutes after ischemia, 0.8–1.2 ml CSF was withdrawn from the cisterna magna, then same amount Soybean oil solution was administered through the cannula. Meanwhile, 40 mg furosemide was administered intravenously.

In group three, at 30 minutes after ischemia, 0.8–1.2 ml CSF was withdrawn from the cistema magna. Meanwhile, saline of 1 ml was administered intravenously.

At 24 hours and one week after ischemic injury, the rabbits were tested for behavioral deficit according to the method in Example One.

The result is summarized as following:

In group one, at 24 hours after ischemia, two rabbits showed a slight behavioral deficit (grade 1–2); three rabbits showed no behavioral deficit (grade 0). At one week after ischemia, all rabbits walked and moved smoothly with no behavioral deficit (grade 0).

In group two, at 24 hours after the ischemia, the rabbits showed behavioral deficit (grade 2–3). At one week after the ischemia, the rabbits remained grade 2–3.

In group three, the rabbits showed complete spastic paraplegia with no movement is to the hind limbs (grade 4) at 24 hours and one week after ischemia.

EXAMPLE 3
Treatment for Brain Ischemia

The global cerebral ischemia was induced in twenty rabbits. Group one: 10 rabbits for Soybean oil treatment. Group two: 10 rabbits for control.

Halothane was given for anesthesia. The trachea was incubated and connected to mechanical intermittent positive-pressure ventilation (tidal volume 30 ml, rate 50/min, $O_2$ concentration 30%). A cannula was surgically positioned in the cisterna magna in each rabbit. A hole of 3 mm in diameter (4 mm lateral to midline and 3 mm posterior to the bregma) was drilled on each side of the skull, a cannula were positioned in the hole on each side through puncture. An arterial line was cannulated through femoral artery for monitoring blood pressure. A femoral vein was also cannulated for withdrawing and infusing blood. Four blood vessels (two common carotid arteries and two vertebrate arteries) were isolated and occluded with arterial clips to produce ischemia. In order to produce complete global ischemia, 60–120 ml of blood was withdrawn to lower the blood pressure simultaneously. The mean blood pressure was maintained between 30–40 mmHg.

In group one, at 5 minutes after the global ischemia, 0.8–1.2 ml of CSF was withdrawn from caunnulas in cisterna magna and holes of the skull, then same amount of soybean oil is administered through the these caunnulas. Meanwhile 40 mg of furosemide was given intravenously.

In group two, at 5 minutes after the global ischemia, 0.8–1.2 ml of CSF was withdrawn from caunnulas in cisterna magna and holes of the skull, then same amount of saline was administered through these caunnulas. Meanwhile 1 ml saline was given intravenously.

At one hours of the global ischemia, the arterial clips were removed and then followed by blood infusion. Phenylephrine (10 mg in 100 ml saline) was given to increase and maintain mean blood pressure between 80–100 mmHg. At 6 hours after ischemic injury, the rabbits were tested for behavioral deficit by the following criteria: Maximum Score=400 (meaning brain death or death); Minimum Score=0 (meaning normal brain)

1. Level of Consciousness
    0=complete awareness of auditory stimuli.
    30=clouded: apparently conscious but drowsy or intermittently irritable on clapping hands and pinching nailbeds of hindlegs.
    60=stupor: response with movements to pinching nailbed of hindlimb, open eyes, movements may be either purposeful or reflex.
    100=coma: no movement on painful stimulation (pinching nailbed of hindlimb; should be confirmed on forelimbs as well).
2. Respiratory Pattern
    0=normal rate and rhythm.
    50=abnormal spontaneous breathing (e.g., periodic gasps, irregular rhythm)
    75=breathing, but not enough to maintain normal arterial blood gases.
    100=apnea: complete absence of spontaneous respiratory efforts
3. Cranial Nerve Function
    Pupil size: examine in room lighting and record diameters of pupil and iris (R/L)
        0=normal: 3–7 mm diameter
        10=abnormal: greater than 7 mm
        15=severely abnormal: greater than 10, pinpoint, or new anisocoria
    Papillary response to light: use flashlight (R/L)
        0=normal
        10=sluggish
        15=absent
    Eyelid reflex:
        0=normal
        10=sluggish
        15=absent
    Corneal reflex: Test with moist cotton swab, observe for eyelid closure (R/L)
        0=normal
        10=sluggish
        15=absent
    Swallow reflex:
        032 normal:
        10=absent
    Auditory-palpebral (startle) reflex: clap hands loudly and observe for motor response
        0=normal
        10=no response
    Gag reflex: stimulate posterior pharynx and observe contraction of the soft palate under direct vision
        0=normal
        10=absent
    Carinal cough reflex: stimulate carina of trachea with suction catheter and observe cough
        0=normal
        10=absent
4. Motor and Sensory Function
    Muscle stretch reflex
        0=normal in all extremities
        10=increased or absent 1–3 extremities
        25=absent in all extremities
    Motor response to painful stimulus: Pinch each limb, observe for withdrawal response.
        0=normal 4
        10=no response
        25=coma (no test required)
    Positioning: place rabbit in left lateral decubitus position and observe position assumed.
        0=normal
        10=mildly abnormal or intermittent running movements
        25=markedly abnormal: opistotonus, fixed flexion, total flaccidity, severe running movements
    Muscle tone: Pick up each extremity and release; observe
        0=normal
        10=1 or 2 extremities stiff or flaccid
        25=3 or 4 extremities stiff or flaccid The results are as follow:

In group one, the average score is from 30–90 (level of consciousness 0–30; respiratory pattern 0; cranial nerve function 0; motor and sensory function 30–60.

In group three, the score is 400. All rabbits died once disconnected from the ventilator.

EXAMPLE 4

Delayed Treatment for Brain Ischemia

The global cerebral ischemia was induced in twelve rabbits according to the method in Example three. Group one: 5 rabbits for 1% Lecithin Vitamin E (1 gram lecithin dissolved in 100 ml of 1 mg/ml Vitamin E injection solution). Group two: 4 rabbits for Vitamin E (1 mg/ml) injection solution. Group three: 3 rabbits for simple CSF withdrawal.

In group one, at 15 minutes after the global ischemia, 0.8–1.2 ml of CSF was withdrawn from caunnulas in cisterna magna and holes of the skull, then same amount of 1% Lecithin Vitamin E injection solution was administered through the these caunnulas. Meanwhile 40 mg of furosemide was given intravenously.

In group two, at 15 minutes after the global ischemia, 0.8–1.2 ml of CSF was withdrawn from caunnulas in cisterna magna and holes of the skull, then same amount of Vitamin E injection solution is administered through the these caunnulas. Meanwhile 40 mg of furosemide was given intravenously.

In group three, at 15 minutes after ischemia, 0.8–1.2 ml CSF was withdrawn from caunnulas in cisterna magna and holes of the skull. Meanwhile, saline of 1 ml was administered intravenously.

At 3 hours and 6 hours after ischemic injury, the rabbits were tested for behavioral deficit by the same criteria mentioned in Example 3:

The results are as follow:

At 3 hours after ischemia: In group one, the scores are 90, 60, 90, 100 and 90 respectively. In group two, the scores are 200, 240, 220 and 220 respectively. In group three, all three rabbits score are 400.

At 6 hours after ischemia: In group one, all five rabbit's scores are 30. In group two, rabbits scores are 90, 100, 90 and 90 respectively. In group three, all rabbits score are 400.

While my above description contains many specifics, these should not be construed as limitations on the scope of the invention, but rather as illustrative examples. In particular, the treatment oil can be any non-toxic organic mixture that is immiscible in water. Similarly, the amphipathic lipid is to be broadly construed and the examples should not be taken as limiting.

What is claimed is:

1. A method for protecting Central Nervous System tissue in need of such protection in a mammal, comprising the steps of:
    a) Withdrawing a volume of cerebrospinal fluid from the subarachnoid space in the region where protection is needed for Central Nervous System tissue,
    b) Injecting a volume of a treatment solution approximately equal to the volume of cerebrospinal fluid withdrawn into said subarachnoid spaces, and
    c) Administering a CSF production-suppressing agent in an amount effective to reduce or stop said CSF production.

2. A method for protecting Central Nervous System tissue in need of such protection according to claim 1 wherein said treatment solution is a solution comprising an amphipathic lipid in oil.

3. A method for protecting Central Nervous System tissue in need of such protection according to claim 1 wherein said treatment solution is a solution consisting essentially of an amphipathic lipid in oil.

4. A method for protecting Central Nervous System tissue in need of such protection according to claim 2 wherein said treatment solution comprises about 1 gram of lecithin per 100 ml. of soybean oil.

5. A method for protecting central nervous system tissue in a mammal according to claim 1 comprising the added step of administering a cellular energy supplying substance.

6. A method for protecting central nervous system tissue in a mammal according to claim 1 comprising the added step of administering an agent that reduces cellular energy requirements.

7. A method for protecting central nervous system tissue according to claim 1 wherein said treatment solution further comprises an osmotic dehydrant.

8. A method for protecting central nervous system tissue according to claim 1 wherein said CSF suppression agent is furosemide.

9. A method for reducing the effects of central nervous system ischemia in a mammal comprising the steps of:
    Withdrawing a volume of cerebrospinal fluid from the subarachnoid space of the central nervous system of the mammal and
    Injecting a volume of a treatment solution approximately equal to the volume of the cerebrospinal fluid withdrawn into said subarachnoid spaces; said treatment solution comprising an amphipathic lipid in oil.

10. A method for treating a central nervous system injury in a mammal requiring such treatment comprising:
    Withdrawing a volume of cerebrospinal fluid from the subarachnoid space of the central nervous system of the mammal, and
    Injecting a volume of a treatment solution approximately equal to the volume of the cerebrospinal fluid withdrawn into said subarachnoid spaces; said treatment solution comprising an amphipathic lipid in oil.

11. A method for screening agents for neuroprotective effect comprising the steps of withdrawing cerebrospinal fluid from the subarachnoid spaces of a living test subject and administering treatment oil comprising an amphipathic lipid in an oil with a proposed neuroprotective agent to said living test subject and determining the effectiveness of said neuroprotective agent.

12. A method for treating a central nervous system injury in a mammal requiring such treatment comprising:
    Withdrawing a volume of cerebrospinal fluid from the subarachnoid space of the central nervous system of the mammal,
    Injecting a volume of a treatment solution comprising an amphipathic lipid in oil approximately equal to the volume of the cerebrospinal fluid withdrawn into said subarachnoid spaces, and
    administering an effective amount of a neuroprotective agent to mammal whereby the therapeutic window of said neuroprotective agent is lengthened.

13. A method for treating a central nervous system injury in a mammal requiring such treatment comprising:
    Withdrawing a volume of cerebrospinal fluid from the subarachnoid space of the central nervous system of the mammal,
    Injecting a volume of a treatment solution comprising an amphipathic lipid in oil approximately equal to the volume of the cerebrospinal fluid withdrawn into said subarachnoid spaces, and
    administering an effective amount of a neuroprotective agent selected from the group consisting of: calcium channel blockers, calcium chelators, potassium channel blockers, free radical scavengers, antioxidants, GABA agonists, GABA receptor antagonists, glutamate antagonists, NMDA antagonists, NMDA channel blockers, glycine site antagonists, polyamine site antagonists, adenosine receptor antagonists, growth factors, Glial cell line derived neurotrophic factor (GDNF), brain derived neurotrophic factor, insulin like growth factor, leukocyte adhesion inhibitors, nitric oxide inhibitors, opiod antagonists, Serotonin agonists, sodium channel blockers, potassium channel openers, anti-inflamatory agents, and protein kinase inhibitors to said mammal whereby the therapeutic window of said neuroprotective agent is lengthened.

14. A method for treating stroke in a mammal requiring such treatment comprising:

Withdrawing a volume of cerebrospinal fluid from the subarachnoid space of the central nervous system of the mammal, injecting a volume of a treatment solution comprising an amphipathic lipid in oil approximately equal to the volume of the cerebrospinal fluid withdrawn into said subarachnoid spaces, and administering a thrombolytic agent to said mammal in an amount effective to restore blood flow to central nervous system tissue.

15. A method according to claim 14 wherein said thrombolytic agent includes recombinant tissue plasminogen activator (rt-PA).

* * * * *